United States Patent [19]

Smucker

[11] 4,209,012
[45] Jun. 24, 1980

[54] KNEE INFLECTION APPARATUS AND METHOD FOR ITS USE

[76] Inventor: Don M. Smucker, 439 E. 2nd St., Perrysburg, Ohio 43551

[21] Appl. No.: 952,667

[22] Filed: Oct. 19, 1978

[51] Int. Cl.² .......................................... A61F 13/00
[52] U.S. Cl. ..................................... 128/133; 269/328
[58] Field of Search .................. 128/133, 134, 94, 31, 128/303 R; 269/328

[56] References Cited

U.S. PATENT DOCUMENTS

| | | | |
|---|---|---|---|
| 1,561,400 | 11/1925 | Begg | 128/133 |
| 2,543,847 | 3/1951 | Hallstedt | 128/94 |
| 2,625,453 | 1/1953 | Lampe et al. | 269/328 |
| 3,776,540 | 12/1973 | Comando | 269/328 |
| 3,791,383 | 2/1974 | Friedman | 128/133 |
| 3,982,742 | 9/1976 | Ford | 269/328 |
| 4,091,808 | 5/1978 | Nelson | 128/133 |

FOREIGN PATENT DOCUMENTS 74992  5/1894  Fed. Rep. of Germany .......... 128/134

Primary Examiner—Lawrence W. Trapp
Attorney, Agent, or Firm—Edward H. Gorman, Jr.

[57] ABSTRACT

An apparatus for use in knee surgery or a related procedure, whereby the patient's knee can be maintained at a predetermined degree of inflection for a desired time interval. The device comprises a foot engaging means attached to an adjustable strap to engage the patient's thigh and a means for fixing the strap length once it has been adjusted. Also disclosed is the method for using the device.

6 Claims, 2 Drawing Figures

KNEE INFLECTION APPARATUS AND METHOD FOR ITS USE

BACKGROUND OF THE INVENTION

1. Field of the Invention

The present invention relates to the field of knee surgery and related procedures. More particularly, it relates to an apparatus for maintaining knee joint inflection in a patient undergoing such surgery or other medical procedure, wherein the knee is held at a fixed or semi-fixed degree of inflection for a desired period of time.

2. Description of the Prior Art

Many surgical procedures involving the knee require that the patient's knee joint be subjected to and maintained at a constant degree of inflection during part or all of the operation. Typical of such procedures are partial or total replacement of an articulating surface such as with a prosthesis, and removal of one or both menisci.

In the performance of such procedures it has heretofore been necessary for the joint to be held in place by an assisting physician or technician in order that the proper degree of inflection be maintained. The present invention is designed to minimize the necessity for this extra physician or technician, thereby both facilitating the performance of the particular surgical procedure, and reducing the number of personnel required.

Various orthopedic and examination devices are known for positioning the limbs of a patient. U.S. Pat. No. 4,091,808 discloses a device for positioning the knee comprising a single strap which forms a loop around the patient's foot, and which closes around the patient's thigh. It differs markedly in structure from the presently disclosed apparatus, as well as suffering from several disadvantages decidedly absent from the present invention. U.S. Pat. No. 3,717,144 discloses a leg supporting device for the upper and lower leg. It comprises separate parts for supporting the upper and lower leg; the parts being pivotable about one another. U.S. Pat. No. 3,776,540 portrays a bed stirrup apparatus for use in pelvic examination whereby the patient's legs are kept far apart. Still another such obstetrical appliance is shown in U.S. Pat. No. 846,648.

The apparatus presently described and claimed provides several additional advantages not provided for in the prior art. Its foot engaging means provides a surface which uniformly encompasses a large part of the patient's foot thus eliminating points of pressure which might otherwise cause pain and irritation. The apparatus permits positioning of the foot such as to achieve tibia rotation and exposure of the posterior part. Because of these and other advantages, the present invention provides a dramatic improvement over any of the other devices heretofore available. Despite the existance of such devices, none has yet been devised having the advantages and utility of the apparatus presently described and claimed.

SUMMARY OF THE INVENTION

The presently disclosed apparatus was invented in order to meet the above-described requirements for maintaining a predetermined degree of knee inflection in a patient during knee surgery. It comprises a foot engaging means, a thigh engaging strap and a means for adjusting the length of that strap. The foot engaging means has a substantially round cross section, i.e. circular, elliptical, etc., and has a foot receiving end into which a patient's foot is inserted, and a foot retaining end to prevent the patient's foot from passing through and out of the engaging means.

Attached to the foot engaging means is a thigh engaging strap. It attaches at two places at or near the foot receiving end, and it attaches in a manner such as to ensure adjustability of its length. Communicating with the strap is a means for fixing its length once the strap has been adjusted to provide a desired degree of inflection.

DETAILED DESCRIPTION OF THE INVENTION

Figure 1:
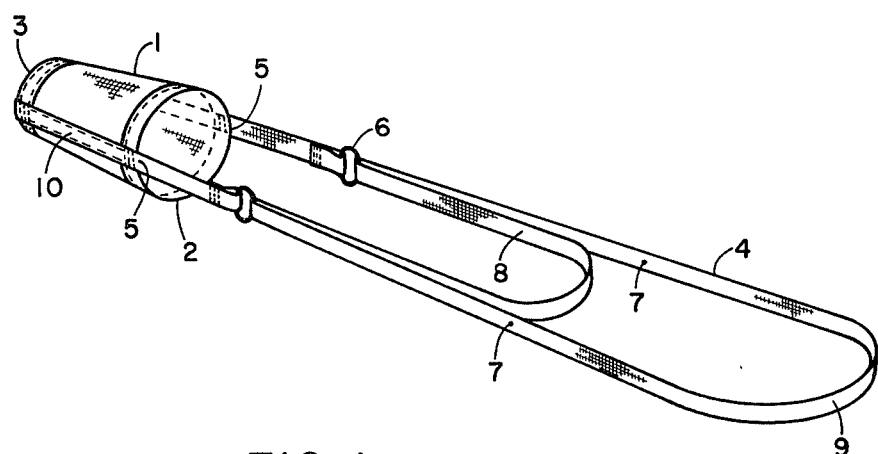
FIG. 1 provides a full view of a preferred embodiment of the apparatus of the present invention.
Figure 2:
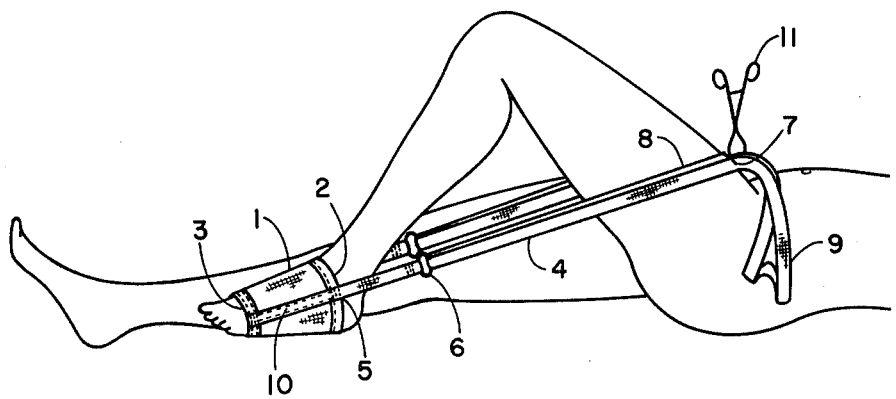
FIG. 2 represents the apparatus in use, and depicts a patient whose knee has been secured at a predetermined degree of knee inflection.

Referring to FIG. 1, foot engaging means 1 is substantially conically shaped, the cone being truncated at foot receiving end 2 and foot retaining end 3. A thigh engaging strap 4 is attached to foot engaging means 1 at its foot receiving end 2 at substantially opposite circumferential positions 5. In the embodiment shown in FIG. 1, strap 4 is a continuous belt, and passes through D-rings 6 which are attached to the foot receiving end of the foot engaging means 1 at circumferential positions 5. A means for fixing the length of strap 4 can be applied at or around points 7 or elsewhere as desired. The embodiment wherein the fixing means is a towel clip is shown in FIG. 2, wherein towel clip 11 is applied at position 7.

The foot engaging means of the present invention can be fabricated from a variety of materials, both synthetic and natural. Thus it can be made of tightly woven cotton or other fabric such as "drill" or "duck", drill being preferred. Alternatively, it could be fabricated from continuous polymer film material, such as polyurethane or a polyolefin. Woven or knitted fabrics of many kinds can be employed; the choice is extensive. Preferably the material chosen for fabricating the foot engaging means should provide flexibility and dimensional integrity and should be comfortable to the ultimate user, the patient.

As stated supra the shape of the foot engaging means 1 is conical, the foot receiving end 2 being somewhat larger in circumference than foot retaining end 3. Thus the patient's foot can slide into the engaging means until it is firmly secured. The flexibility of the material permits the engaging means to uniformly surround the patient's foot, thus eliminating any points of pressure, chafing or other irritation. Moreover, the dimensional integrity of the material precludes stretching and assures that the patient's knee will remain at the desired degree of inflection throughout the particular surgical procedure. Thus the necessity of an extra person to hold a patient throughout an operation is eliminated.

The thigh engaging strap, like the foot engaging means, can be made from a variety of materials, a cotton or synthetic webbing, drill or duck being particularly suitable. All that is necessary is that the strap be flexible, that it not stretch appreciably while in use, and that it be adjustable. For example, it can be a long strip of webbing attached by both of its ends to the foot engaging means. Alternatively, it can comprise a continuous belt 4 as depicted in FIG. 1. In this embodiment it can pass through D-rings 6 to form an inner loop 8 and an outer loop 9. Inner loop 8 engages the patient's thigh, whereas outer loop 9 can be secured by a suitable length adjusting means.

An adjusting means is provided in the present invention for fixing the thigh engaging strap at a predetermined length, thereby simultaneously fixing knee inflection. The adjusting means can take on various known configurations, such as a snap fastener, buckle or other means. In a preferred embodiment, such as shown in FIGS. 1 and 2, it takes on the form of towel clip 11 which immovably engages the strap at positions 7.

The following Examples are provided to further illustrate and teach the present invention. They are intended solely for those purposes, and are not to be interpreted as limiting the invention in any way.

Example I—Fabricating a Preferred Embodiment

A piece of drill fabric obtained from Continental Textile Corporation of St. Louis, Mo., was cut into a strip measuring 9½ inches by 7 inches. The strip was then hemmed along the 7 inch dimension on each side using heavy cotton thread, the hem measuring about 1½ inches in width. The hemmed drill measured about 6 inches by about 7 inches. The hemmed drill was then trimmed from one hem to the other at a bias, such that, after trimming, one hem measured 7 inches while the opposite hem measured 5 inches. This resulted in a regular trapezoid of drill, one hem parallel to and centered above the other.

Another drill trapezoid was similarly fabricated and the two sewn together, one on top of the other, along the non-hemmed, biased edges. The stitching was made ½ inch from the edge, thus leaving two ½ inch overhangs on each biased edge. This resulted in a truncated cone of drill having a foot receiving end 2 measuring 12 inches in circumference and a foot receiving end 3 of 8 inches in circumference.

Next, strips of webbing were sewn onto the truncated cone along sides 10 where the ½ inch overhangs occurred. The strips of webbing were obtained in rolls measuring 1½ inches in width available from T. T. Connolly Co., Chicago, Il. The ½ inch overhangs were spread apart, thus forming a ridge, over which the webbing strips were applied. Each strip measured 10 inches by 1½ inches and was sewn flush with the foot retaining end 3 and extending 4 inches beyond the foot receiving end 2.

D-rings 6 were secured to the ends of webbing extending beyond the foot receiving end. The D-rings measured 1½ inches and were made of stainless steel. They are easily commercially available. They were secured, one on each webbing end, by passing the webbing end through a D-ring and stitching the webbing to itself.

When both D-rings were secured, a thigh strap was attached by running another length of the same 1½ inch webbing through both D-rings. The strap measured 120 inches in length, and, after being passed through the D-rings, was joined at its ends and sewn together into a continuous belt.

In use, the thigh engaging strap of this apparatus was adjusted by means of an ordinary towel clip 11 (FIG. 2) available in most hospital operating rooms and available from numerous surgical supply houses.

Example II—Total Knee Arthroplasty Using the Apparatus

The device of Example I was utilized in performing a total knee arthroplasty. The patient's foot was placed into the foot engaging means 1 by insertion into receiving end 2. Next strap 4 was doubled to form inner loop 8 and outer loop 9 (FIG. 1) and both loops were positioned over the patient's thigh substantially above his knee (FIG. 2).

The initial incision was then made with a scalpel followed by the insertion of gelpis to spread and retain the incised tissue. Once the capsule has been cut and the knee joint opened, the knee was bent and loop 9 was adjusted until loop 8 had tightened about the patient's thigh enough to provide sufficient knee inflection. Loop 9 was then clamped with a towel clip to assure a fixed length, and a correspondingly fixed degree of inflection.

When the articular condiles of the knee were removed and the bone ends sculptured and fitted for the prosthesis, outer loop 9 was further tightened and the towel clip repositioned accordingly. This provided still further knee inflection. The articular surfaces of the knee were then sculptured to permit insertion of the prosthesis. The leg was then permitted to extend by removing towel clip 11 thereby releasing strap 4 and rendering it free to elongate. This permitted testing of the prosthesis prior to cementing in the implants.

After the prosthesis has been tested, the knee was again inflexed by adjusting loop 9 and securing it with towel clip 11. The implants were then cemented in place with methylmethacrylate cement in the femoral and tibial compartments. The knee inflection device was left in place to insure minimal motion while the cement was setting, after which the device was loosened and the leg extended to test the implants for stability. Once stability was assured, the inflection device was removed and closure was performed.

What is claimed is:

1. An apparatus for maintaining a predetermined degree of knee joint inflection in a patient during knee surgery, said apparatus comprising
    a substantially truncated cone-shaped foot engaging means having a foot receiving end and a foot retaining end, said receiving end having a circumference larger than said retaining end, and the axial length of said foot engaging means being at least sufficient to accept and position said patient's foot,
    a thigh engaging strap for engaging said patient's thigh, said strap being affixed to said receiving end of said foot engaging means at substantially opposite circumferential positions of said receiving end, and
    means for fixedly adjusting the length of said thigh engaging strap.

2. The apparatus of claim 1 wherein said thigh engaging strap is a continuous belt of flexible material.

3. The apparatus of claim 2 wherein said strap is affixed to said receiving end by means of two D-rings attached to said receiving end at substantially opposite circumferential positions, said continuous belt passing through each of said D-rings.

4. The apparatus of any of claims 1, 2 or 3 wherein said strap length fixing means is a towel clip.

5. An apparatus for maintaining a predetermined degree of knee joint inflection in a patient during surgery comprising a foot engaging means comprising a truncated cone of flexible material, having a foot receiving end and a foot retaining end, said foot receiving end being of a larger circumference than said foot retaining end, said receiving end having two D-rings affixed thereto, each at a substantially opposite circumferential position from the other;

a thigh engaging strap comprising a continuous loop of flexible material, said loop being movably affixed to said foot engaging means at said D-rings by passing through each of said D-rings; and a towel clip communicating with said thigh engaging strap for fixing said strap at a predetermined length.

6. A method for maintaining a predetermined degree of knee joint inflection in a patient during surgery, said method comprising inserting the foot of said patient into the foot receiving end of the foot engaging means of the apparatus of claims 1, 2, 3 or 5, positioning said thigh engaging strap over the thigh of said patient, adjusting the length of said strap until said predetermined degree of knee joint inflection has been attained, and fixing the length of said strap, thereby maintaining said predetermined degree of knee joint inflection.

* * * * *